US00PP26488P2

(12) United States Plant Patent
Heuger

(10) Patent No.: US PP26,488 P2
(45) Date of Patent: Mar. 8, 2016

(54) ***HELLEBORUS* PLANT NAMED 'COSEH 3050'**

(50) Latin Name: ***Helleborus niger*×*Helleborus argutifolius***
Varietal Denomination: COSEH 3050

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 199 days.

(21) Appl. No.: 13/999,075

(22) Filed: Jan. 10, 2014

(51) Int. Cl.
*A01H 5/00* (2006.01)

(52) U.S. Cl.
USPC ..... Plt./439

(58) Field of Classification Search
USPC ..... Plt./439
See application file for complete search history.

*Primary Examiner* — Anne Grunberg
(74) *Attorney, Agent, or Firm* — C. A. Whealy

(57) ABSTRACT

A new and distinct cultivar of *Helleborus* plant named 'COSEH 3050', characterized by its upright and mounding plant habit; uniform and freely flowering habit; dark green-colored leaves; freely and early flowering habit; single white and yellow green-colored flowers; and good garden performance.

2 Drawing Sheets

Botanical designation: *Helleborus niger*×*Helleborus argutifolius.*

Cultivar denomination: 'COSEH 3050'.

BACKGROUND OF THE INVENTION

The present invention relates to a new and distinct cultivar of *Helleborus* plant, botanically known as *Helleborus niger*× *Helleborus argutifolius* and hereinafter referred to by the name 'COSEH 3050'.

The new *Helleborus* plant is a product of a planned breeding program conducted by the Inventor in Glandorf, Germany. The objective of the breeding program was to create new uniform *Helleborus* plants with unique and attractive plant habit, leaf and flower coloration and resistance to pests common to *Helleborus* plants.

The new *Helleborus* plant originated from a cross-pollination conducted by the Inventor in Glandorf, Germany in December, 2007 of an unnamed proprietary seedling selection of *Helleborus niger*, not patented, as the female, or seed, parent with an unnamed proprietary seedling selection of *Helleborus argutifolius*, not patented, as the male, or pollen, parent. The new *Helleborus* plant was discovered and selected by the Inventor as a single flowering plant from within the progeny of the stated cross-pollination grown in a controlled greenhouse environment in Glandorf, Germany in October, 2009.

Asexual reproduction of the new *Helleborus* plant by divisions in a controlled environment in Glandorf, Germany since February, 2010 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'COSEH 3050'. These characteristics in combination distinguish 'COSEH 3050' as a new and distinct *Helleborus* plant:

1. Upright and mounding plant habit.
2. Uniform and freely flowering habit.
3. Dark green-colored leaves.
4. Freely and early flowering habit.
5. Single white and yellow green-colored flowers.
6. Good garden performance.

Compared to plants of the parent selections, plants of the new *Helleborus* are more uniformly mounded and are more freely flowering.

Plants of the new *Helleborus* can be compared to plants of *Helleborus niger*×*Helleborus argutifolius* 'COSEH 830', disclosed in U.S. Plant Pat. No. 22,348. In side-by-side comparisons conducted in Glandorf, Germany, plants of the new *Helleborus* differed primarily from plants of 'COSEH 830' in the following characteristics:

1. Plants of the new *Helleborus* were more freely flowering than plants of plants of 'COSEH 830'.
2. Plants of the new *Helleborus* flowered earlier than plants of 'COSEH 830'.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet comprises a side perspective view of a typical flowering plant of 'COSEH 3050' grown in a container.

The photograph on the second sheet is a close-up view of a typical flower of 'COSEH 3050'.

DETAILED BOTANICAL DESCRIPTION

The aforementioned photographs and following observations, measurements and values describe plants grown during the autumn in 17-cm containers in a glass-covered greenhouse in Glandorf, Germany and under cultural practices typical of commercial *Helleborus* production. During the production of the plants, day temperatures ranged from 12° C. to 32° C. and night temperatures ranged from 3° C. to 18° C. Plants were 14 months old when the photographs and the description were taken. In the following description, color references are made to The Royal Horticultural Society Colour Chart, 2007 Edition, except where general terms of ordinary dictionary significance are used.

Botanical classification: *Helleborus niger*×*Helleborus argutifolius* 'COSEH 3050'.

Parentage:

*Female, or seed, parent*.—Unnamed proprietary seedling selection of *Helleborus niger*, not patented.

*Male, or pollen, parent*.—Unnamed proprietary seedling selection of *Helleborus argutifolius*, not patented.

Propagation:

*Type*.—By tissue culture.

*Time to initiate roots, winter*.—About two months at temperatures about 12° C.

*Time to produce a rooted young plant, winter*.—About six months at temperatures ranging from 4° C. to 15° C.

*Root description*.—Thick to thin, fleshy; white to brown in color.

*Rooting habit*.—Sparse.

Plant description:

*Plant and growth habit*.—Herbaceous perennial; upright and mounding plant habit with flowers held just above the foliar plane; plant shape is roughly globular; moderately vigorous growth habit.

*Plant height, soil level to top of foliar plane*.—About 19.7 cm.

*Plant height, soil level to top of flowers*.—About 24.4 cm.

*Plant diameter* (*area of spread*).—About 49.3 cm.

Leaf description:

*Arrangement*.—Leaves arranged in a basal rosette; leaves palmately compound with five leaflets per leaf.

*Leaf length*.—About 18.6 cm.

*Leaf width*.—About 26.9 cm.

*Leaflet length*.—About 14.7 cm.

*Leaflet width*.—About 5 cm.

*Leaf shape*.—Palmate; reniform in outline.

*Leaflet shape*.—Narrowly ovate to narrowly obovate, slightly curved.

*Leaflet apex*.—Acute to narrowly acute.

*Leaflet base*.—Attenuate.

*Leaflet margin*.—Serrate.

*Leaflet texture, upper and lower surfaces*.—Smooth, glabrous; leathery.

*Leaflet luster, upper surface*.—Moderately glossy.

*Leaflet luster, lower surface*.—Slightly glossy.

*Leaflet venation pattern*.—Pinnate.

*Leaflet color*.—Developing leaves, upper surface: Between N137A and 147A. Developing leaves, lower surface: Between 146B and 147B. Fully developed leaves, upper surface: Darker than between 139A and 147A; venation, close to 144A. Fully developed leaves, lower surface: Close to 147B; venation, close to 145A.

*Petioles*.—Length: About 12.7 cm. Diameter: About 7 mm. Texture, upper and lower surfaces: Smooth, glabrous. Color, upper and lower surfaces: Close to 145A.

Flower description:

*Flower shape and habit*.—Single rotate flowers in terminal racemes; freely and uniform flowering habit with about ten flowers per raceme and about 80 flowers developing per plant; flowers facing outwardly to slightly nodding.

*Fragrance*.—None detected.

*Natural flowering season*.—Plants begin flowering about ten months after planting; plants flower from autumn into winter in Germany.

*Flower longevity on the plant*.—About ten days; flowers not persistent.

*Inflorescence height*.—About 20.7 cm.

*Inflorescence diameter*.—About 29.1 cm.

*Flower buds*.—Length: About 2 cm. Diameter: About 1.25 cm. Shape: Ovate. Color: Close to 145C; under surface tinged with close to 145B.

*Flower diameter*.—About 7.7 cm.

*Flower depth* (*height*).—About 2.3 cm.

*Petals*.—Transformed into nectaries.

*Sepals*.—Quantity and arrangement: Five, arranged in a single whorl. Length: About 3.6 cm. Width: About 2.7 cm. Shape: Ovate. Apex: Bluntly acute. Base: Broadly cuneate. Margin: Entire. Texture, upper and lower surfaces: Smooth, glabrous. Color: When opening, upper surface: Between 150C and 150D; towards the margins, close to 150D; center and towards the base, close to 145A. When opening, lower surface: Close to 145C; towards the margins, close to 150D; towards the base, close to 145A. Fully opened, upper surface: Between 150D and 155A; center and towards the base, close to 150D and 145C; at the base, close to 145B. Fully opened, lower surface: Close to 145C to 145D; towards the margins, close to 150D; towards the base, close to 145A to 145B.

*Peduncles*.—Length: About 10.9 cm. Diameter: About 7 mm. Aspect: About 30° from vertical. Strength: Moderately strong. Texture: Smooth, glabrous. Color: Close to 144B to 144C; basally, moderately speckled with close to 183D.

*Pedicels*.—Length: About 2.9 cm. Diameter: About 2 mm. Aspect: About 30° from peduncle axis. Strength: Moderately strong. Texture: Smooth, glabrous. Color: Close to 145C tinged with close to 182D.

*Reproductive organs*.—Stamens: Quantity per flower: About 90. Filament length: About 1.6 cm. Filament color: Close to NN155D. Anther shape: Reniform; basifixed. Anther length: About 2 mm. Anther color: Close to 3C. Pollen amount: Scarce. Pollen color: Close to 4D. Pistils: Quantity per flower: About five to eight. Pistil length: About 1 cm. Stigma shape: Club-shaped. Stigma color: Close to 155A. Style length: About 9.5 mm. Style color: Close to 155A. Ovary color: Close to 150C to 150D. Nectaries (transformed petals): Quantity per flower: About 13. Length: About 9 mm. Diameter: About 2 mm. Shape: Tubular, flattened. Color, immature, inner and outer surfaces: Close to 144C. Color, mature, inner and outer surfaces: Close to 144B; towards the apex and base, close to N144A; with development, color becoming closer to 144A and towards the apex and base, close to 151A.

*Seeds and fruits*.—Seed and fruit development have not been observed on plants of the new *Helleborus*.

Garden performance: Plants of the new *Helleborus* have been observed to have good garden performance and to tolerate rain, wind and high temperatures about 35° C. and to be hardy to USDA Hardiness Zone 5.

Pathogen & pest resistance: Plants of the new *Helleborus* have not been observed to be resistant to pathogens and pests common to *Helleborus* plants.

It is claimed:

1. A new and distinct *Helleborus* plant named 'COSEH 3050' as illustrated and described.

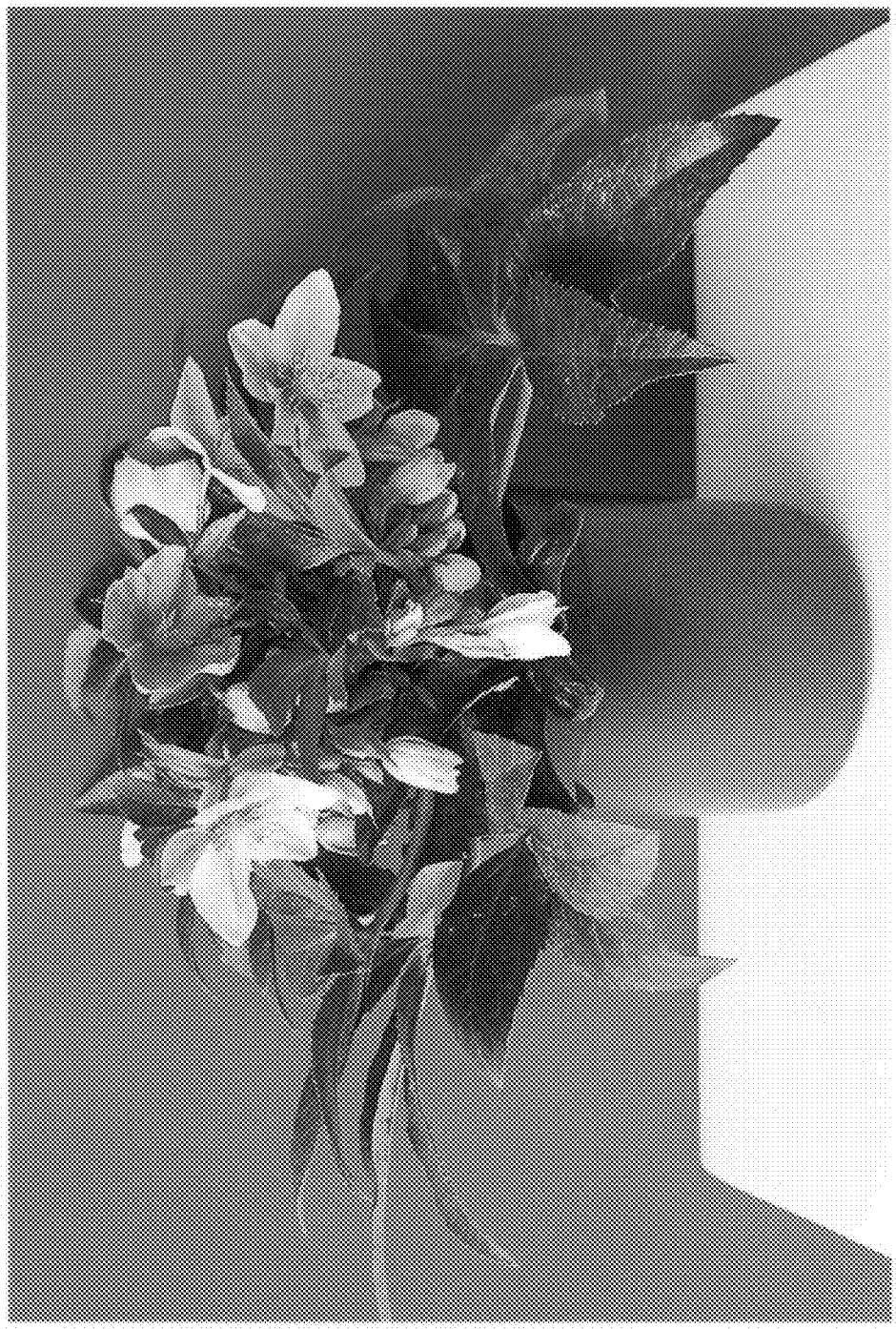

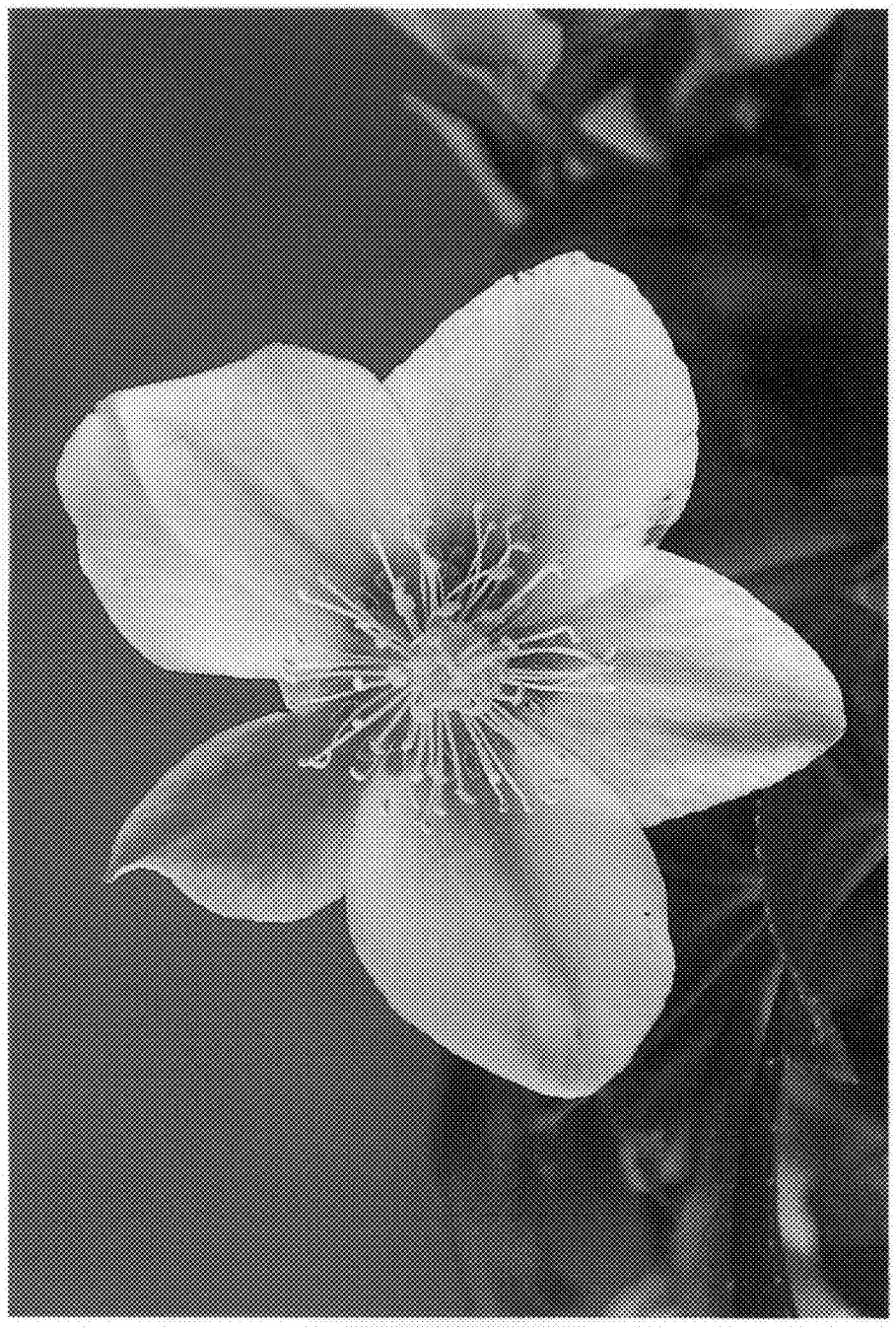

* * * * *